(12) United States Patent
Ward et al.

(10) Patent No.: US 7,972,828 B2
(45) Date of Patent: Jul. 5, 2011

(54) STABILIZED COMPOSITIONS OF THERMOSTABLE DNA POLYMERASE AND ANIONIC OR ZWITTERIONIC DETERGENT

(75) Inventors: Brian W. Ward, St. Louis, MO (US);
Ernest J. Mueller, St. Louis, MO (US);
Jessica Copeland, St. Louis, MO (US);
Deborah Vassar, St. Louis, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 75 days.

(21) Appl. No.: 11/612,776

(22) Filed: Dec. 19, 2006

(65) Prior Publication Data
US 2008/0145910 A1   Jun. 19, 2008

(51) Int. Cl.
*C12N 9/96* (2006.01)
*C12N 9/12* (2006.01)

(52) U.S. Cl. ............................... 435/193; 435/6

(58) Field of Classification Search .................. None
See application file for complete search history.

(56) References Cited

U.S. PATENT DOCUMENTS

| | | | |
|---|---|---|---|
| 4,682,195 A | 7/1987 | Yilmaz | |
| 4,683,202 A | 7/1987 | Mullis | |
| 4,800,159 A | 1/1989 | Mullis et al. | |
| 5,489,523 A | 2/1996 | Mathur | |
| 5,556,772 A | 9/1996 | Sorge et al. | |
| 5,612,473 A * | 3/1997 | Wu et al. .................. 536/25.42 |
| 5,871,975 A * | 2/1999 | Kacian et al. ................ 435/91.2 |
| 6,127,155 A | 10/2000 | Gelfand et al. | |
| 6,242,235 B1 * | 6/2001 | Shultz et al. .................. 435/194 |
| 6,617,136 B2 | 9/2003 | Parthasarathy et al. | |
| 2008/0096262 A1 * | 4/2008 | Kobayashi et al. .......... 435/193 |

FOREIGN PATENT DOCUMENTS

| WO | 8906691 A2 | 7/1989 |
| WO | 9209689 A1 | 6/1992 |
| WO | WO2004869451 * | 10/2004 |
| WO | WO20040869451 * | 10/2004 |
| WO | 2008013885 A2 | 1/2008 |

OTHER PUBLICATIONS

Henke et al., Nucleic Acids Research, 1997, 25(19), p. 3957-3958.*
Aldrich entry 473197, 2008.*
International Search Report for PCT/US07/87887 dated Sep. 24, 2008; 5 pages.
Yang et al., "Use of multiplex polymerase chain reactions to indicate the accuracy of the annealing temperature of thermal cycling", Analytical Biochemistry, 2005, pp. 192-200, vol. 338.
Supplementary European Search Report for EP07865796 dated Mar. 17, 2011, 8 pages.

* cited by examiner

*Primary Examiner* — Stephanie K Mummert
(74) *Attorney, Agent, or Firm* — Polsinelli Shughart PC

(57) ABSTRACT

The present invention provides compositions, methods, and kits for protecting thermostable DNA polymerase during amplification reactions conducted at a temperature ranging from about 40° C. to greater than 100° C. The composition comprises a thermostable DNA polymerase and an anionic detergent or zwitterionic detergent.

14 Claims, 3 Drawing Sheets

STABILIZED COMPOSITIONS OF THERMOSTABLE DNA POLYMERASE AND ANIONIC OR ZWITTERIONIC DETERGENT

FIELD OF THE INVENTION

The present invention provides compositions, methods, and kits comprising compositions of thermostable DNA polymerase and an anionic detergent or zwitterionic detergent.

BACKGROUND OF THE INVENTION

Many widely known recombinant DNA techniques involve replicating or amplifying DNA. One such example is the polymerase chain reaction (PCR). During PCR, a thermostable DNA polymerase cycles repeatedly between low and high temperatures (e.g., 55° C. and 95° C.). The total period of time spent at the high temperature depends upon the total number of cycles, the duration of the high temperature step of each cycle, and the ramp speed (i.e., the speed at which the thermocycler switches between the steps of each cycle). Although these DNA polymerases are highly thermostable, they tend to become inactive at high temperatures over time. Furthermore, these enzymes may also be inactivated by dilution into aqueous environments with sub-optimal concentration of cofactors or sub-optimal pH levels, and the presence of chemical or biological inhibitors in the reaction mixtures.

One way of stabilizing an enzyme is to add a stabilizing agent, such as a surfactant. Surfactants, or detergents, are surface-active compounds that stabilize the interface between the active form of an enzyme and the liquid environment in which they are contained. The activity of Taq DNA polymerase has been stabilized by the addition of nonionic detergents, such as Tween 20. In some applications, however, Tween 20-stabilized DNA polymerases have low efficiencies of amplification or lead to the amplification of non-specific products. There is a need, therefore, for detergents that improve the stability of thermostable DNA polymerases in solution, and particularly detergents that improve enzyme stability without imparting any of the disadvantages of currently used detergents.

SUMMARY OF THE INVENTION

One aspect of the invention encompasses a composition comprising a thermostable DNA polymerase and an anionic detergent. Alternatively, the composition may comprise a thermostable DNA polymerase and a zwitterionic detergent.

Yet another aspect of the invention provides a method for inhibiting inactivation of a thermostable DNA polymerase in a thermal cycling process. The method comprises contacting the DNA polymerase with an anionic detergent or zwitterionic detergent during the thermal cycling process.

Another aspect of the invention encompasses a kit for inhibiting inactivation of a thermostable DNA polymerase in a thermal cycling process. The kit comprises a thermostable DNA polymerase and an anionic detergent or a zwitterionic detergent.

Other aspects and features of the invention are described in more detail herein.

FIGURES

Figure 1:
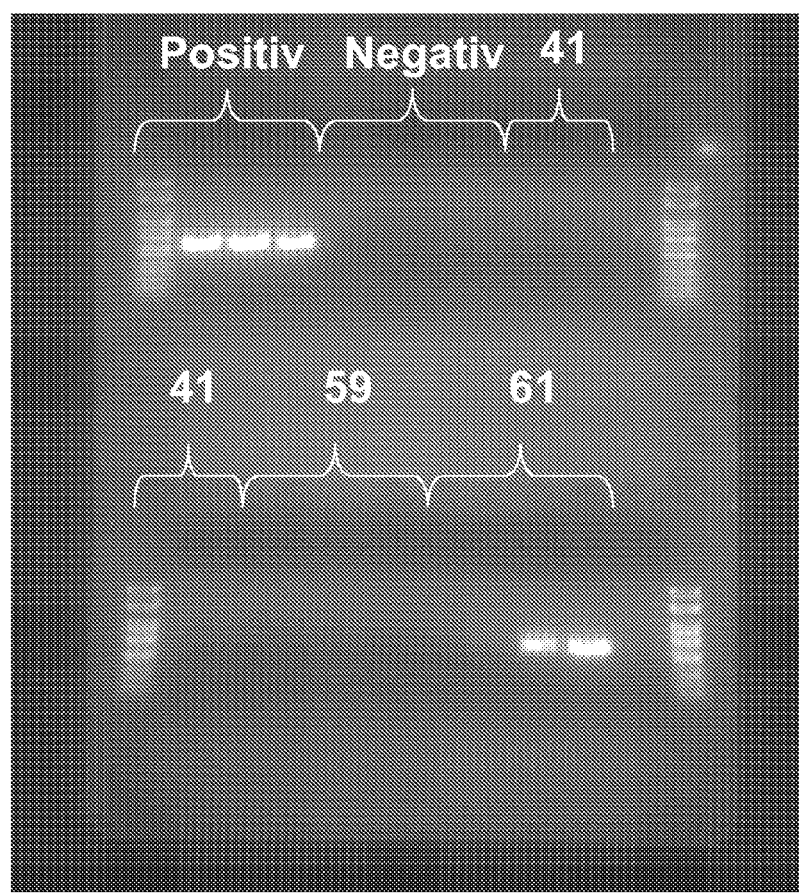

FIG. 1 is a photographic image of fluorescently-stained PCR fragments resolved on an agarose gel. The leftmost and rightmost lanes each contain a DNA ladder. Each of the lanes labeled "positive" contain a 500 bp fragment that was amplified in the presence of 0.0005% Tween 20. The lanes labeled "negative" represent reactions performed in the absence of a stabilizing detergent. The lanes labeled "41" represent reactions performed in the presence of 0.05%, 0.05%, 0.005%, and 0.0005%, from left to right, of carrageenan lambda. The lanes labeled "59" represent reactions performed in the presence of 0.05%, 0.05%, 0.005%, and 0.0005%, from left to right, of Mackanate™ DOS-70. The lanes labeled "61" represent reactions performed in the presence of 0.05%, 0.05%, 0.005%, and 0.0005%, from left to right, of Rhodafac RM710.

Figure 2:
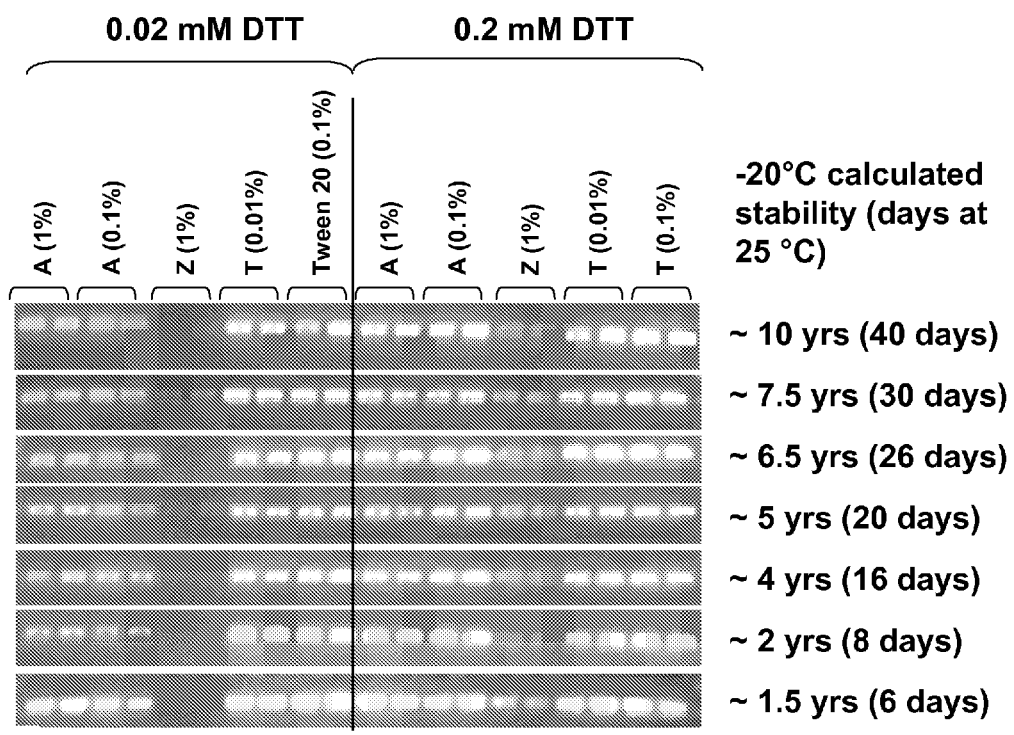

FIG. 2 is a photographic image of fluorescently-stained PCR fragments resolved on an agarose gel. The bright bands correspond to a 500 by fragment amplified with Taq DNA polymerase formulated with different concentration of the anionic (A) detergent, poly(ethylene glycol) 4-nonylphenyl 3 sulfopropyl ether potassium salt, the zwitterionic (Z) detergent, CHAPS, or Tween 20 (T). The different formulations were stored in the presence of different concentrations of DTT for different periods of time, as indicated at the right.

Figure 3:
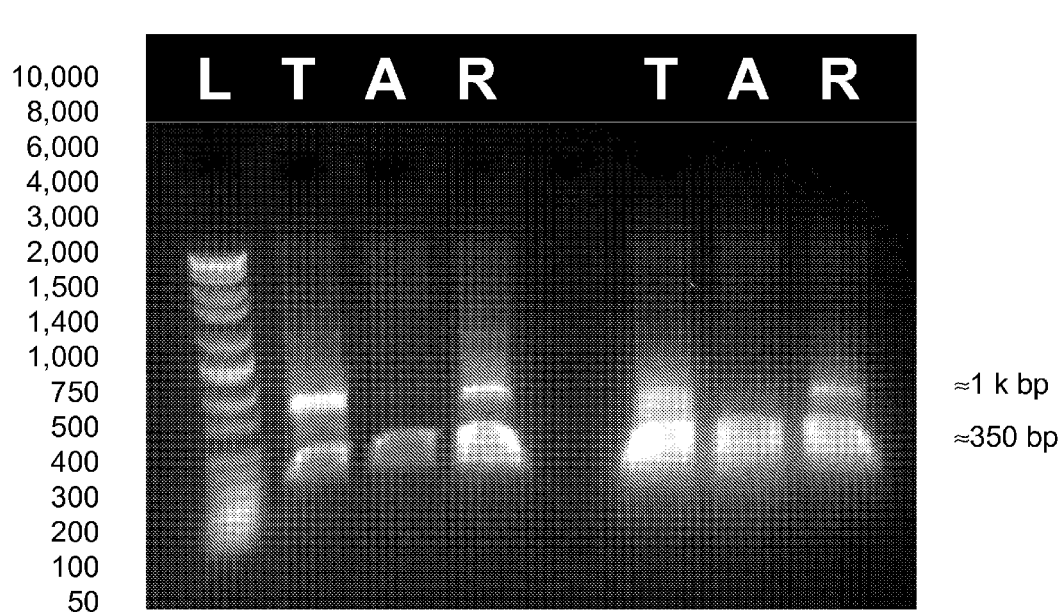

FIG. 3 is a photographic image of fluorescently-stained PCR fragments resolved on an agarose gel. The lane labeled "L" contains a DNA ladder, with the size of the fragments denoted to the left of the image. The three lanes on the left represent reactions in which a 352 by fragment was targeted for amplification, and the three lanes on the right represent reactions in which a 360 by fragment was targeted for amplification. The lanes labeled "T" contain fragments amplified with Taq DNA polymerase formulated with Tween 20. Each of the lanes labeled "A" contains a fragment amplified by Taq DNA polymerase formulated with the anionic surfactant, poly(ethylene glycol) 4-nonylphenyl 3-sulfopropyl ether potassium salt. The lanes labeled "R" contain fragments amplified with another commercially available Tween 20 formulated Taq DNA polymerase.

DETAILED DESCRIPTION OF THE INVENTION

While substantially thermostable, DNA polymerases, such as Taq, do become inactive over time at the high temperatures utilized in thermal cycling reactions. It has been discovered, as demonstrated in the examples, that thermostable DNA polymerases may be protected from such heat inactivation by contacting the polymerase with either an anionic detergent or a zwitterionic detergent during a thermal cycling process. Accordingly, the present invention provides compositions, methods and kits for inhibiting inactivation of a thermostable DNA polymerase during thermal cycling processes. In its most basic form, the composition of the invention comprises a thermostable DNA polymerase and either an anionic detergent or zwitterionic detergent. Suitable compositions are detailed below.

It is envisioned that the compositions of the invention will be utilized to protect thermostable DNA polymerases during thermocycling processes (e.g., PCR) used to amplify a target nucleic acids. While the target nucleic acid will typically be DNA, it is also envisioned in some embodiments that the target nucleic acid may be RNA or a mixture of DNA and RNA. In the event that RNA is to be used as a template, enzymes, and/or conditions optimal for reverse transcribing the template to DNA known to those in the art would be utilized. Preferably, the target nucleic acid is DNA.

A preferred method of target nucleic acid amplification is PCR. Briefly, PCR amplification involves an enzymatic chain reaction in which exponential quantities of the target nucleic acid are produced relative to the number of reaction steps performed. PCR amplification is generally conducted at a temperature ranging from about 50° C. to about 95° C. for approximately one to about fifty cycles and more typically from about ten to about forty cycles. PCR amplification techniques and many variations of the PCR are known and well documented. The compositions of the invention may be utilized to protect thermostable DNA polymerase in PCR and in variations of PCR. See e.g., Saiki et al., Science 239: 487-491 (1988); U.S. Pat. Nos. 4,682,195, 4,683,202 and 4,800,159, all of which are hereby incorporated by reference in their entirety.

I. Thermostabilized Compositions

The composition of the invention comprises an anionic detergent and a thermostable DNA polymerase. Alternatively, the composition comprises a zwitterionic detergent and a thermostable DNA polymerase. The composition may further comprise a buffering agent, a monovalent salt, a divalent salt, a reducing agent, a chelating agent, and a mixture of dNTPs. Reaction mixtures comprising a composition of the invention may further comprise reactants for DNA amplification reactions.

a. Anionic Detergent

The composition of the invention may comprise an anionic detergent. Suitable anionic detergents include compounds that inhibit inactivation of thermostable DNA polymerase when it is subjected to repeated amplification reactions conducted at high temperatures (e.g., 50° C. to 95° C.). Methods for determining whether particular anionic detergent compound functions in this manner are detailed in the Examples. Suitable anionic detergents are detailed below or are otherwise known in the art.

Suitable anionic detergents may be selected from the group consisting of alkyl sulfates, alkyl sulfonates, alkyl benzene sulfonates, alpha sulfonyl fatty acids, alkyl phosphates, dioctyl sulfosuccinate, isethionates, alkyl ether sulfates, methyl sarcosines and the like. Representative examples of suitable anionic detergents include amine dodecylbenzene sulfonate; ammonium capryleth sulfate; ammonium cumenesulfonate; ammonium dihydroxy stearate; ammonium dodecylbenzene sulfonate; ammonium laureth sulfate; ammonium laureth-12 sulfate; ammonium laureth-30 sulfate; ammonium lauroyl sarcosinate; ammonium lauryl sulfate; ammonium lauryl sulfosuccinate; ammonium lignosulfonate; ammonium myreth sulfate; ammonium naphthalene sulfonate; ammonium nonoxynol-20 sulfate; ammonium nonoxynol-30 sulfate; ammonium nonoxynol-4 sulfate; ammonium nonoxynol-6 sulfate; ammonium nonoxynol-9 sulfate; ammonium oleic sulfate; ammonium perfluorooctanoate; ammonium stearate; ammonium xylenesulfonate; butyl naphthalene sulfonate; butyl phosphate; calcium dodecylbenzene sulfonate; calcium stearoyl lactylate; calcium tetrapropylenebenzene sulfonate; capryleth-9 carboxylic acid; cetyl phosphate; cumene sulfonic acid; DEA-cetyl phosphate; DEA-dodecylbenzene sulfonate; DEA-lauryl sulfate; deceth-4 phosphate; diammonium lauryl sulfosuccinate; diammonium stearyl sulfosuccinamate; diamyl sodium sulfosuccinate; dicyclohexyl sodium sulfosuccinate; dihexyl sodium sulfosuccinate; diisobutyl sodium sulfosuccinate; dilaureth-7 citrate; dimethiconol; dinonoxynol-4 phosphate; dioctyl ammonium sulfosuccinate; dioctyl sodium sulfosuccinate; disodium cetearyl sulfosuccinamate; disodium cocamido MEA-sulfosuccinate; disodium cocamido PEG-3 sulfosuccinate; disodium deceth-6 sulfosuccinate; disodium decyl diphenyl ether disulfonate; disodium dodecyloxy propyl sulfosuccinamate; disodium isodecyl sulfosuccinate; disodium laneth-5 sulfosuccinate; disodium lauramido DEA-sulfosuccinate; disodium lauramido MEA-sulfosuccinate; disodium laureth sulfosuccinate; disodium lauryl sulfosuccinate; disodium myristamido MEA-sulfosuccinate; disodium oleamido MEA-sulfosuccinate; disodium oleamido PEG-2 sulfosuccinate; disodium oleth-3 sulfosuccinate; disodium PEG-4 cocamido MIPA sulfosuccinate; disodium ricinoleamido MEA-sulfosuccinate; disodium stearyl sulfosuccinamate; disodium undecylenamido MEA-sulfosuccinate; ditridecyl sodium sulfosuccinate; dodecenylsuccinic anhydride; dodecyl diphenyl ether disulfonic acid; dodecyl diphenyloxide disulfonic acid; dodecylbenzenesulfonic acid; glyceryl dioleate SE; glyceryl distearate SE; glyceryl ricinoleate SE; glyceryl stearate citrate; glyceryl stearate SE; glycol stearate SE; hexyl phosphate; isopropyl phosphate; isopropylamine dodecylbenzenesulfonate; isosteareth-2 phosphate; isotrideceth-3 phosphate; isotrideceth-6 phosphate; laureth-1 phosphate; laureth-12 carboxylic acid; laureth-3 phosphate; laureth-4 phosphate; laureth-6 phosphate; laureth-7 citrate; laureth-9 phosphate; lauryl phosphate; lithium lauryl sulfate; magnesium laureth sulfate; magnesium PEG-3 cocamide sulfate; MEA-laureth phosphate; MEA-lauryl sulfate; MIPA-laureth sulfate; MIPA-lauryl sulfate; myristoyl sarcosine; naphthalene-formaldehyde sulfonate; nonoxynol-10 phosphate; nonoxynol-12 phosphate; nonoxynol-3 phosphate; nonoxynol-4 phosphate; nonoxynol-4 sulfate; nonoxynol-6 phosphate; nonoxynol-7 phosphate; nonoxynol-8 phosphate; nonoxynol-9 phosphate; nonyl nonoxynol-10 phosphate; nonyl nonoxynol-15 phosphate; nonyl nonoxynol-7 phosphate; oleth-10 carboxylic acid; oleth-10 phosphate; oleth-3 carboxylic acid; oleth-4 phosphate; oleth-5 phosphate; oleth-6 carboxylic acid; oleth-7 phosphate; PEG-2 dilaurate SE; PEG-2 dioleate SE; PEG-2 distearate SE; PEG-2 laurate SE; PEG-2 oleate SE; PEG-2 stearate SE; PEG-9 stearamide carboxylic acid; potassium cetyl phosphate; potassium deceth-4 phosphate; potassium dodecylbenzene sulfonate; potassium isosteareth-2 phosphate; potassium lauroyl sarcosinate; potassium lauryl sulfate; potassium oleate; potassium oleic sulfate; potassium perfluorooctoate; potassium ricinoleic sulfate; PPG-2 laurate SE; PPG-2 oleate SE; PPG-2 stearate SE; PPG-5-ceteth-10 phosphate; propylene glycol laurate SE; propylene glycol oleate SE; propylene glycol ricinoleate SE; propylene glycol stearate SE; PVM/MA copolymer; sodium 2-ethylhexyl phosphate; sodium 2-ethylhexyl sulfate; sodium a olefin sulfonate; sodium allyloxy hydroxypropyl sulfonate; sodium behenoyl lactylate; sodium butoxyethoxy acetate; sodium butyl naphthalene sulfonate; sodium butyl oleate sulfate; sodium butyl oleate sulfonate; sodium butyl phosphate; sodium caproyl lactylate; sodium caprylyl sulfonate; sodium cetyl sulfate; sodium cumenesulfonate; sodium deceth sulfate; sodium decyl diphenyl ether sulfonate; sodium decyl sulfate; sodium dibutyl naphthalene sulfonate; sodium didodecylbenzene sulfonate; sodium diisooctyl sulfosuccinate; sodium diisopropyl naphthalene sulfonate; sodium dilaureth-7 citrate; sodium dinonyl sulfosuccinate; sodium dodecyl diphenyl ether disulfonate; sodium dodecyl diphenyloxide disulfonate; sodium dodecylbenzenesulfonate; sodium glyceryl trioleate sulfate; sodium hexadecyl diphenyl disulfonate; sodium hexadecyl diphenyloxide disulfonate; sodium hexyl diphenyloxide disulfonate; sodium isethionate; sodium isodecyl sulfate; sodium isooctyl sulfate; sodium isostearoyl lactylate; sodium isotrideceth-15 sulfate; sodium lactate; sodium lauramido DEA-sulfosuccinate; sodium laureth phosphate; sodium laureth sulfate; sodium laureth sulfosuccinate; sodium laureth-10 phosphate; sodium laureth-11 carboxylate; sodium laureth-12 sulfate; sodium laureth-13 acetate; sodium laureth-13 carboxylate; sodium laureth-3 carboxylate; sodium laureth-4 carboxylate; sodium laureth-4 phosphate; sodium laureth-6 carboxylate;

sodium laureth-7 carboxylate; sodium laureth-7 sulfate; sodium laureth-8 sulfate; sodium lauroyl glutamate; sodium lauroyl lactylate; sodium lauroyl lactylate; sodium lauroyl methylaminopropionate; sodium lauroyl sarcosinate; sodium lauryl phosphate; sodium lauryl sulfate; sodium lauryl sulfoacetate; sodium lignate; sodium lignosulfonate; sodium methallyl sulfonate; sodium methyl lauroyl taurate; sodium methyl myristoyl taurate; sodium methyl oleoyl taurate; sodium methyl palmitoyl taurate; sodium methyl stearoyl taurate; sodium methylnaphthalenesulfonate; sodium m-nitrobenzenesulfonate; sodium myreth sulfate; sodium myristoyl glutamate; sodium myristoyl sarcosinate; sodium myristyl sulfate; sodium nonoxynol sulfate; sodium nonoxynol-10 sulfate; sodium nonoxynol-10 sulfosuccinate; sodium nonoxynol-15 sulfate; sodium nonoxynol-4 sulfate; sodium nonoxynol-5 sulfate; sodium nonoxynol-6 phosphate; sodium nonoxynol-6 sulfate; sodium nonoxynol-8 sulfate; sodium nonoxynol-9 phosphate; sodium nonoxynol-9 sulfate; sodium octoxynol-2 ethane sulfonate; sodium octoxynol-3 sulfate; sodium octyl sulfate; sodium octylphenoxyethoxyethyl sulfonate; sodium oleic sulfate; sodium oleth-7 phosphate; sodium oleyl phosphate; sodium oleyl sulfate; sodium oleyl sulfosuccinamate; sodium palmitoyl sarcosinate; sodium phenyl sulfonate; sodium propyl oleate sulfate; sodium stearoyl lactylate; sodium stearyl sulfosuccinamate; sodium trideceth sulfate; sodium trideceth-3 carboxylate; sodium trideceth-6 carboxylate; sodium trideceth-7 carboxylate; sodium tridecyl sulfate; sodium tridecylbenzene sulfonate; sodium xylenesulfonate; stearoyl sarcosine; TEA-lauroyl glutamate; TEA-lauryl sulfate; tetrasodium dicarboxyethyl stearyl sulfosuccinamate; TIPA-laureth sulfate; triceteareth-4 phosphate; triceteth-5 phosphate; trideceth-2 phosphate; trideceth-3 phosphate; trideceth-5 phosphate; tridecyl phosphate; and trilaureth-4 phosphate; trioctyl phosphate.

In yet another embodiment, the anionic detergent may be selected from the group consisting of glycolic acid ethoxylate octyl ether; glycolic acid ethoxylate oleyl ether; glycolic acid ethoxylate lauryl ether; poly(ethylene glycol) 4-nonylphenyl 3-sulfopropyl ether potassium salt; glycolic acid ethoxylate 4-tert-butylphenyl ether; glycolic acid ethoxylate oleyl ether; glycolic acid ethoxylate oleyl ether; poly(ethylene glycol) n-alkyl 3-sulfopropyl ether potassium salt; glycolic acid ethoxylate 4-nonylphenyl ether; poly(ethylene glycol) n-alkyl 3-sulfopropyl ether potassium salt; sodium cholate hydrate; sodium deoxycholate; sodium taurodeoxycholate hydrate; sodium taurocholate; sodium cholate hydrate; sodium deoxycholate; sodium taurodeoxycholate hydate; sodium taurocholate; glycolic acid ethoxylate octyl ether; glycolic acid ethoxylate oleyl ether; glycolic acid ethoxylate lauryl ether; poly(ethylene glycol)4-nonylphenyl 3-sulfopropyl ether potassium salt; glycolic acid ethoxylate 4-tert-butylphenyl ether; glycolic acid ethoxylate oleyl ether; glycolic acid ethoxylate oleyl ether; poly(ethylene glycol) n-alkyl 3-sulfopropyl ether potassium salt; glycolic acid ethoxylate 4-nonylphenyl ether; and poly(ethylene glycol) n-alkyl 3-sulfopropyl ether potassium salt.

In an exemplary embodiment, the anionic detergent is selected from the group consisting of poly(ethylene glycol) 4-nonphenyl 3-sulfopropyl ether potassium salt; poly(ethylene glycol) monolaurate; polyoxyethylene(150)dinonylphenyl ether (Igepal® DM-970); and nonyl nonoxynol-15 phosphate (Rhodafac RM710).

b. Zwitterionic Detergent

Alternatively, the composition of the invention may comprise a zwitterionic detergent. Suitable zwitterionic detergents include compounds that inhibit inactivation of thermostable DNA polymerase when it is subjected to repeated amplification reactions conducted at high temperatures (e.g., 50° C. to 95° C.). Methods for determining whether particular zwitterionic detergent compound functions in this manner are detailed in the Examples. Suitable zwitterionic detergents are detailed below or are otherwise known in the art.

In one embodiment, the zwitterionic detergent may be a compound comprising formula (Ia):

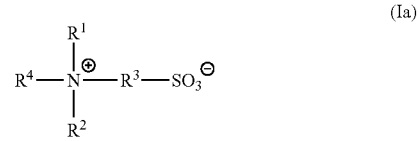

(Ia)

wherein:

$R^1$, $R^2$, $R^3$, and $R^4$ are independently hydrocarbyl or substituted hydrocarbyl.

Typically, for compounds having formula (Ia) each of $R^1$, $R^2$, and $R^3$ will consist of a chain of no more than about 1 to 10 atoms, more preferably a chain of about 1 to 7 atoms, still more preferably, a chain of no more than 1 to 5 atoms and even more preferably, a chain of no more than 1 to 3 atoms. In most embodiments for compounds having formula (Ia), $R^4$ will consist of a chain of no more than about 5 to 30 atoms, more preferably, a chain of about 8 to about 25 atoms, and still more preferably, will be a chain of about 10 to about 20 atoms. Exemplary compounds having formula (Ia) will have a chain of about 1 to 5 atoms for each of $R^1$, $R^2$, and $R^3$ and a chain of about 8 to 20 atoms for $R^4$. Even more exemplary compounds having formula (Ia) will have a methyl group for each of $R^1$ and $R^2$, a chain from about 1 to 3 atoms for $R^3$ and a chain from about 10 to 16 atoms for $R^4$.

A further embodiment encompasses zwitterionic detergents comprising a compound of formula (Ib):

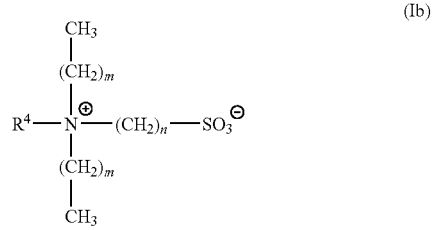

(Ib)

wherein:

m is an integer from 0 to 10;

n is an integer from 1 to 10; and $R^4$ is a hydrocarbyl or substituted hydrocarbyl.

Generally speaking, in most embodiments for compounds having formula (Ib), m is an integer from 0 to 5, n is an integer from 1 to 8 and $R^4$ has a chain length of from about 8 to 25 atoms. In a more exemplary alternative of this embodiment, m is an integer from 0 to 3, n is an integer from 1 to 5 and $R^4$ has a chain length of from about 10 to 20 atoms. In an even more exemplary alternative of this embodiment, m is 0, n is 3 and $R^4$ has a chain length from about 10 to 16 atoms.

Yet another embodiment encompasses a zwitterionic detergent comprising a compound of (Ic):

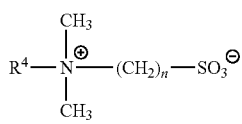

wherein:
n is an integer from 1 to 10; and
$R^4$ is a hydrocarbyl or substituted hydrocarbyl.

Typically for compounds having formula (Ic), n is an integer from 1 to 8 and $R^4$ has a chain length of from about 8 to 25 atoms. In a more exemplary alternative of this embodiment, n is an integer from 1 to 5 and $R^4$ has a chain length of from about 10 to 20 atoms. In an even more exemplary alternative of this embodiment, n is 3 and $R^4$ has a chain length from about 10 to 16 atoms.

In still another embodiment, the zwitterionic detergent may be a compound comprising formula (Id):

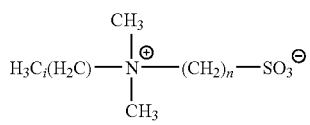

wherein:
i is an integer from 8 to 25; and
n is an integer from 1 to 10.

Generally speaking, in most embodiments for compounds having formula (Id), i is an integer from 10 to 20 and n is an integer from 1 to 5. In an exemplary embodiment, i is an integer from 10 to 16 and n is 3.

Representative exemplary zwitterionic detergent compounds having formula (Ia), (Ib), (Ic), or (Id) include:
3-(N,N-Dimethyltetradecylammonio)propanesulfonate (SB3-14);
3-(4-Heptyl)phenyl-3-hydroxypropyl)dimethylammonio-propanesulfonate (C7BzO);
CHAPS (3-[(3-cholamidopropyl)dimethylammonio]-1-propanesulfonate);
CHAPSO (3-[(3-cholamidopropyl)dimethylammonio]-2-hydroxy-1-propanesulfonate);
3-(decyldimethylammonio) propanesulfonate inner salt (SB3-10);
3-(dodecyldimethylammonio) propanesulfonate inner salt (SB3-12);
3-(N,N-dimethyloctadecylammonio) propanesulfonate (SB3-18);
3-(N,N-dimethyloctylammonio) propanesulfonate inner salt (SB3-8); 3-(N,N-dimethylpalmitylammonio) propanesulfonate (SB3-16); and
3-[N,N-dimethyl(3-myristoylaminopropyl)ammonio]propanesulfonate (ASB-14).

In a particularly preferred embodiment for compounds having formula (Ia), (Ib), (Ic), or (Id), the zwitterionic detergent is CHAPS or CHAPSO. CHAPS has the following chemical structure:

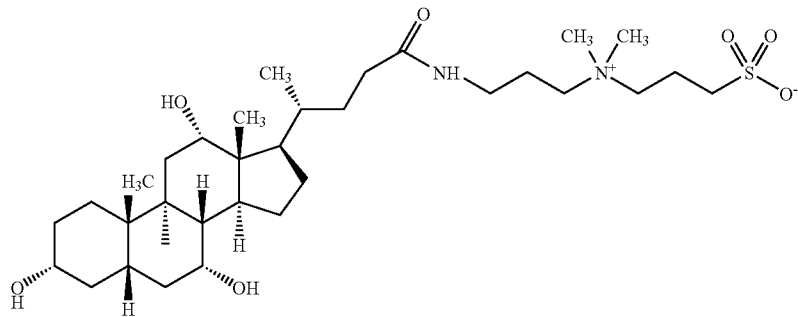

wherein n is an integer between 18 and 22. In an exemplary embodiment n is 20.

CHAPSO has the following chemical structure:

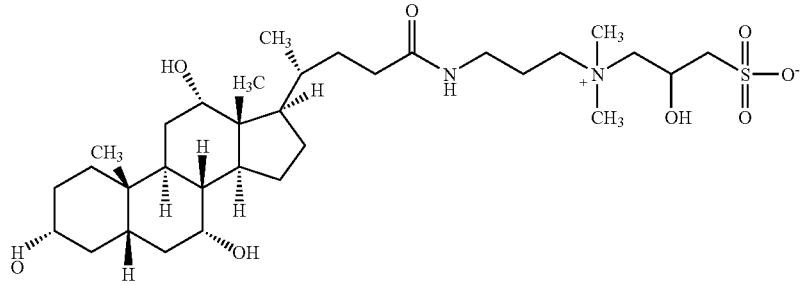

Other suitable zwitterionic detergents, depending on the embodiment, include: acetylated lecithin; apricotamidopropyl betaine; babassuamidopropyl betaine; behenyl betaine; bis 2-hydroxyethyl tallow glycinate; C12-14 alkyl dimethyl betaine; canolamidopropyl betaine; capric/caprylic amidopropyl betaine; capryloamidopropyl betaine; cetyl betaine; cocamidopropyl betaine; cocamidopropyl dimethylaminohydroxypropyl hydrolyzed collagen; N-[3-cocamido)-propyl]-N,N-dimethyl betaine, potassium salt; cocamidopropyl hydroxysultaine; cocamidopropyl sulfobetaine; cocaminobutyric acid; cocaminopropionic acid; cocoamphodipropionic acid; coco-betaine; cocodimethylammonium-3-sulfopropylbetaine; cocoiminodiglycinate; cocoiminodipropionate; coco/oleamidopropyl betaine; cocoyl sarcosinamide DEA; DEA-cocoamphodipropionate; dihydroxyethyl tallow glycinate; dimethicone propyl PG-betaine; N,N-dimethyl-N-lauric acid-amidopropyl-N-(3-sulfopropyl)-ammonium betaine; N,N-dimethyl-N-myristyl-N-(3-sulfopropyl)-ammonium betaine; N,N-dimethyl-N-palmityl-N-(3-sulfopropyl)-ammonium betaine; N,N-dimethyl-N-stearamidopropyl-N-(3-sulfopropyl)-ammonium betaine; N,N-dimethyl-N-stearyl-N-(3-sulfopropyl)-ammonium betaine; N,N-dimethyl-N-tallow-N-(3-sulfopropyl)-ammonium betaine; disodium caproamphodiacetate; disodium caproamphodipropionate; disodium capryloamphodiacetate; disodium capryloamphodipropionate; disodium cocoamphodiacetate; disodium cocoamphodipropionate; disodium isostearoamphodipropionate; disodium laureth-5 carboxyamphodiacetate; disodium lauriminodipropionate; disodium lauroamphodiacetate; disodium lauroamphodipropionate; disodium octyl b-iminodipropionate; disodium oleoamphodiacetate; disodium oleoamphodipropionate; disodium PPG-2-isodeceth-7 carboxyamphodiacetate; disodium soyamphodiacetate; disodium stearoamphodiacetate; disodium tallamphodipropionate; disodium tallowamphodiacetate; disodium tallowiminodipropionate; disodium wheatgermamphodiacetate; N,N-distearyl-N-methyl-N-(3-sulfopropyl)-ammonium betaine; erucamidopropyl hydroxysultaine; ethylhexyl dipropionate; ethyl hydroxymethyl oleyl oxazoline; ethyl PEG-15 cocamine sulfate; hydrogenated lecithin; hydrolyzed protein; isostearamidopropyl betaine; lauramidopropyl betaine; lauramidopropyl dimethyl betaine; lauraminopropionic acid; lauroamphodipropionic acid; lauroyl lysine; lauryl betaine; lauryl hydroxysultaine; lauryl sultaine; linoleamidopropyl betaine; lysolecithin; milk lipid amidopropyl betaine; myristamidopropyl betaine; octyl dipropionate; octyliminodipropionate; oleamidopropyl betaine; oleyl betaine; 4,4(5H)-oxazoledimethanol, 2-(heptadecenyl)-; palmitamidopropyl betaine; palmitamine oxide; ricinoleamidopropyl betaine; ricinoleamidopropyl betaine/IPDI copolymer; sesamidopropyl betaine; sodium C12-15 alkoxypropyl iminodipropionate; sodium caproamphoacetate; sodium capryloamphoacetate; sodium capryloamphohydroxypropyl sulfonate; sodium capryloamphopropionate; sodium carboxymethyl tallow polypropylamine; sodium cocaminopropionate; sodium cocoamphoacetate; sodium cocoamphohydroxypropyl sulfonate; sodium cocoamphopropionate; sodium dicarboxyethyl cocophosphoethyl imidazoline; sodium hydrogenated tallow dimethyl glycinate; sodium isostearoamphopropionate; sodium lauriminodipropionate; sodium lauroamphoacetate; sodium oleoamphohydroxypropylsulfonate; sodium oleoamphopropionate; sodium stearoamphoacetate; sodium tallamphopropionate; soyamidopropyl betaine; stearyl betaine; tallowamidopropyl hydroxysultaine; tallowamphopolycarboxypropionic acid; trisodium lauroampho PG-acetate phosphate chloride; undecylenamidopropyl betaine; and wheat germamidopropyl betaine.

c. Thermotolerant Enzyme

The stabilized composition of the invention may comprise a variety of enzymes that catalyze reactions involving nucleic acids at elevated temperatures-particularly thermal cycling processes (e.g., PCR). Enzymes that modify, cut, or synthesize nucleic acids may be stabilized in the compositions of the invention. Examples include ligase, phosphodiesterase, DNase, exonuclease, RNase, phosphatase, kinase, terminal transferase, reverse transcriptase, restriction endonuclease, RNA polymerase, and DNA polymerase. In an exemplary embodiment, the enzyme is a thermostable polymerase that catalyzes the amplification of a target polynucleotide sequence. A thermostable DNA polymerase is particularly preferred.

Generally speaking, suitable thermostable DNA polymerases are substantially stable at elevated temperatures and efficiently catalyze amplification of a target polynucleotide in a thermal cycling process. In this context, the thermostable DNA polymerase is substantially resistant to inactivation when subjected to the elevated temperatures for the time necessary to effect denaturation of double-stranded nucleic acids. Inactivation, as utilized herein, refers to permanent and complete loss of enzymatic activity. While it is envisioned that the temperature necessary for nucleic acid denaturation will depend on a variety of factors (e.g., on the buffer salt concentration and the length and nucleotide composition of the nucleic acids being denatured), the temperature will typically range from about 90° C. to about 105° C. As such, suitable thermostable DNA polymerases typically do not become inactivated at a temperature of about 90° C. to temperatures greater than about 100° C. Additionally, the thermostable DNA polymerase also typically has an optimum temperature at which it functions that is higher than about 40° C., which is the temperature below which hybridization of primers to the DNA template is promoted. Exemplary thermostable DNA polymerases, as such, typically function throughout the entire temperature spectrum utilized in thermal cycling reactions, such as PCR. For example, suitable thermostable DNA polymerases generally have an optimum temperature range from about 40° C. to 110° C., and more typically, from about 50° C. to about 95° C.

The thermostable DNA polymerase may be obtained from any source and may be a native or recombinant protein. Representative heat-stable polymerases are the DNA polymerases isolated from the thermophilic bacteria *Thermus flavus, Thermus ruber, Thermus thermophilus, Bacillus stearothermophilus, Thermus aquaticus, Thermus lacteus, Thermus rubens*, and *Methanothermus fervidus*. Thermostable polymerases isolated from the thermophilic archaebacteria include, for example, *Sulfolobus solfataricus, Sulfolobus acidocaldarius, Thermoplasma acidophilum, Methanobacterium thermoautotrophicum* and *Desulfurococcus mobilis*. An exemplary thermostable DNA polymerase is isolated from *Thermus aquaticus* (Taq). Various strains of Taq DNA polymerase are known in the art including from the American Type Culture Collection, Rockville, Md., and is described by T. D. Brock, J. Bact. (1969) 98:289-297, and by T. Oshima, Arch. Microbiol. (1978): 189-196. Taq DNA polymerase is also commercially available from a variety of sources.

As will be appreciated by a skilled artisan, a combination of two or more of the above thermostable polymerases such as, for example, a combination of Taq and Pfu, may also be used in the processes of the present invention.

d. Combinations of Detergent and Thermostable DNA Polymerase

The composition of the invention includes any combination of anionic detergent described in I(a) or otherwise known in the art and any of the thermostable DNA polymerases described in I(c) or otherwise known in the art. Alternatively, the composition may include any combination of zwitterionic detergent described in I(b) or otherwise known in the art and any of the thermostable DNA polymerases described in I(c) or otherwise known in the art. Exemplary combinations of anionic detergents or zwitterionic detergent and thermostable DNA polymerase are depicted in Table A.

TABLE A

| Detergent | DNA Polymerase |
| --- | --- |
| poly(ethylene glycol)4-nonphenyl 3-sulfopropyl ether potassium salt | Taq |
| poly(ethylene glycol) monolaurate | Taq |
| Igepal ® DM-970 | Taq |
| Rhodafac RM710 | Taq |
| 3-(N,N-Dimethyltetradecylammonio)propanesulfonate | Taq |
| 3-(4-Heptyl)phenyl-3-hydroxypropyl)dimethylammoniopropanesulfonate | Taq |
| CHAPS | Taq |
| CHAPSO | Taq |
| 3-(decyldimethylammonio) propanesulfonate inner salt | Taq |
| 3-(dodecyldimethylammonio) propanesulfonate inner salt | Taq |
| 3-(N,N-dimethyloctadecylammonio) propanesulfonate | Taq |
| 3-(N,N-dimethyloctylammonio) propanesulfonate inner salt | Taq |
| (N,N-dimethylpalmitylammonio) propanesulfonate | Taq |
| 3-[N,N-dimethyl(3-myristoylaminopropyl)ammonio]propanesulfonate | Taq |

The concentration of thermostable DNA polymerase utilized to catalyze a given DNA amplification reaction can and will vary depending upon the reaction parameters. Typically, Taq DNA polymerase formulations are provided at about 0.1 unit/µL to about 5 units/µL. The concentration of Taq DNA polymerase in a amplification reaction mixture may range from about 0.01 unit/µL to about 0.1 unit/µL.

The amount of anionic detergent or zwitterionic detergent present in a composition of the invention can and will vary. Generally speaking, the amount utilized will typically be an amount effective to produce the desired result (e.g., inhibit inactivation of DNA polymerase). The detergent, for example, may be present in the composition at a concentration from about 0.0005% to about 2% by weight, preferably from about 0.001% to about 1% by weight, and more preferably from about 0.005% to about 0.1% by weight.

e. Additional Agents

In addition to a detergent (i.e., anionic or zwitterionic) and a thermostable DNA polymerase, the composition of the invention may further comprise a buffering agent, a monovalent salt, a divalent salt, a reducing agent, a chelating agent, and a mixture of dNTPs. Reaction mixtures comprising a composition of the invention may further comprise reactants for DNA amplification reactions.

Suitable buffering agents include those known in the art that are utilized in thermal cycling processes. Depending on the embodiment, the buffering agent may be a storage buffer or a reaction buffer. Irrespective of the embodiment, typically the buffering agent will maintain the pH of the composition from about 4.0 to about 9.5, more typically from about 6.0 to about 9.0 and still more typically from about 7.0 to about 8.0.

Representative examples of suitable buffering agents include MOPS, HEPES, TAPS, Bicine, Tricine, TES, PIPES, MES, or a Tris buffer. A storage buffer may further comprise a storage solution such as glycerol.

The composition may also include a salt. In one embodiment, the salt may be a monovalent salt. Suitable monovalent salts include sodium chloride, potassium chloride, or lithium chloride. Alternatively, the salt may be a divalent salt. Representative examples of suitable divalent salts include calcium chloride or magnesium chloride.

The composition may further comprise a reducing agent. Suitable reducing agents include dithiothreitol, β-mercaptoethanol, sodium borohydride, oxalic acid, or lithium aluminium hydride. The concentration of the reducing may be higher than that typically added to enzyme compositions. In additional embodiments, the composition may include a chelating agent. Examples of suitable chelating agents include EDTA or EGTA.

In additional embodiments, the composition may further comprise a mixture of dNTPs selected from dATP, dCTP, dGTP, and dTTP.

Reaction mixtures comprising the composition may also comprise reactants for DNA amplification reactions. Typically, reactants for DNA amplification reactions will include, in addition to a thermostable DNA polymerase, a target polynucleotide, a mixture of dNTPs, and a pair of oligonucleotide primers. Reactions mixtures may comprise an additional buffering agent, monovalent salt, and divalent salt for optimal enzyme activity. Optionally, the mixture may also include a reagent to increase efficiency of PCR. Suitable examples of such agents include dimethyl sulfoxide, formamide, and betaine.

II. Kits

This invention also contemplates kits for inhibiting inactivation, and in particular, heat inactivation, of a thermostable DNA polymerase in the thermal cycling process. Such kits may include, for example, the a thermostable DNA polymerase and either an anionic detergent or zwitterionic detergent. The kit may further comprise a reducing agent, a buffering agent, a mixture of dNTPs, and instructions for using the composition and other components necessary for thermal cycling reactions to amplify nucleic acids. The kit may be in the form of a test kit of controls, that is, in a packaged collection or combination as appropriate for the needs of the user and any analytical instrumentation involved. The kit can, of course, also include appropriate packaging, containers, labeling, buffers, and controls for thermal cycling reactions to amplify nucleic acids.

DEFINITIONS

To facilitate understanding of the invention, a number of terms are defined below:

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The "amplification" of nucleic acids refers to the replication of one to many additional copies of a nucleic acid sequence by a method catalyzed by an enzyme. Preferably, it is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR and other primer extension methodologies, a primer refers to a short oligonucleotide of defined sequence that is annealed to a nucleic acid template to provide an initiation site for a polymerase as in the polymerase chain reaction.

"Complimentary" refers to the natural association of nucleic acid sequences by base-pairing (5'-A G T-3' pairs with the complimentary sequence 3'-T C A-5'). Complementarity between two single-stranded molecules may be partial, if only some of the nucleic acids pair are complimentary, or complete, if all bases pair are complimentary.

The term "dNTP" refers to deoxynucleoside triphosphates. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring.

The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

A "polymerase" is a catalyst, usually a protein enzyme, for forming an extension of an oligonucleotide along a DNA template where the extension is complimentary to the template. A "polymerase" is an enzyme that is capable of incorporating nucleoside triphosphates to extend a 3' hydroxyl group of a nucleic acid molecule, if that molecule has hybridized to a suitable template nucleic acid molecule. Polymerase enzymes are discussed in Watson, J. D., In: Molecular Biology of the Gene, 3rd Ed., W. A. Benjamin, Inc., Menlo Park, Calif. (1977), which reference is incorporated herein by reference, and similar texts.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorus, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Detergent Screening

A PCR assay was used to screen 47 of the potential candidate detergents for their ability to stabilize Taq DNA polymerase. The final concentration of each detergent tested was 5%, 0.5%, 0.05%, 0.005%, or 0.0005%. A forward primer (5'-TGGATACCCGTCGTGGCTCTAATT-3'; SEQ ID No:1) and a reverse primer (5'-CTTCTTTCGTCCCCGTCAG-GCTGA-3'; SEQ ID No:2) were designed to amplify a 500 bp fragment of lambda DNA. Each 10 μl reaction contained:

1 µl 10×PCR Buffer
0.2 µl 10 mM dNTPs
1 µl 10 µM Forward Primer
1 µl 10 µM Reverse Primer
1 µl ~5 ng/µl lambda DNA
1 µl 10× detergent (50%, 5%, 0.5%, 0.05%, 0.005%)
4.7 µl dH$_2$O
0.1 µl 5 Units/µl Taq DNA polymerase The cycling parameters were 94° C. for 15 min and 30 cycles of 94° C. for 30 sec and 70° C. for 30 sec, and a 4° C. hold. For each series of detergents tested, positive control reactions comprising 0.0005% Tween 20 were included, as well as negative control reactions without any detergent. An aliquot of each reaction was resolved by agarose gel electrophoresis. A representative gel is shown in FIG. 1. Amplified products were present in the positive control reactions, as well as in reactions with a low concentration of the detergent nonyl nonoxynol-15 phosphate (Rhodafac RM710).

These screening reactions revealed that the following detergents supported PCR: 3-[(3-cholamidopropyl) dimethylammonio]-1-propanesulfonate hydrate (CHAPS), 3-([3-cholamidopropyl]dimethylammonio)-2-hydroxy-1-propanesulfonate (CHAPSO), poly(ethylene glycol)4-nonphenyl 3-sulfopropyl ether potassium salt; poly(ethylene glycol) monolaurate; polyoxyethylene(150)dinonylphenyl ether (Igepal® DM-970); and nonyl nonoxynol-15 phosphate (Rhodafac RM710).

Example 2

Stabilization of Taq Formulations with DTT

The long-term stability of Taq formulated with either Tween 20, an anionic detergent, or a zwitterionic detergent was compared in the presence of two concentrations of DTT. Taq was formulated with 0.01% or 0.1% Tween 20, 0.1% or 1% poly(ethylene glycol) 4-nonylphenyl 3 sulfopropyl ether potassium salt, or 1% CHAPS. Each formulation was stored in the presence of 0.02 mM DTT or 0.2 mM DTT at 25° C. for periods of time ranging from 6 days to 40 days. The calculated corresponding periods for storage at −20° C. ranged from about 1.5 years to about 10 years (see FIG. 2). The ability of various formulations of Taq to support PCR was assessed using a PCR assay similar to that described in Example 1. The same primers and reactions conditions were used.

An aliquot of each reaction was resolved by agarose gel electrophoresis. Representative gel images are shown in FIG. 2. The Tween 20 formulations were essentially unaffected by storage time at both DTT concentrations. The zwitterionic (Z) detergent formulations were substantially able to support PCR in the presence of the higher concentration of DTT. At the higher concentration of DTT, all of the anionic (A) detergent formulations were able to support PCR at all the times tested. These data indicate that supplemental DTT further stabilized formulations comprising an anionic or zwitterionic detergent.

Example 3

Amplification Efficiency with Tween 20 or Anionic Detergent Formulated Preparations The efficiency of amplification by Taq DNA polymerase in the presence of Tween 20 or the anionic detergent, poly (ethylene glycol) 4-nonylphenyl 3 sulfopropyl ether potassium salt, was compared using SYBR Green quantitative real-time PCR (qPCR) to amplify four different fragments in MseI-digested or intact human genomic DNA. Primers used to amplify 14-3-3, CD14F, HOXA2, and PGK1 are presented in Table 1. Each reaction comprised 1× Jumpstart Taq Ready mix (Sigma Aldrich, St. Louis, Mo.) formulated with Tween 20 or poly (ethylene glycol) 4-nonylphenyl 3 sulfopropyl ether potassium salt, 1×ROX (reference dye), 0.8×SYBR green, 0.4 µM primers. The template was serially diluted such that reactions contained 25 ng, 2.5 ng, or 0.25 ng of intact DNA or 400 ng, 40 ng, of 4 ng of digested DNA. The cycling profile was 95° C. for 3 min, 35 cycles of 95° C. for 30 sec, 55° C. for 60 sec, and 72° C. for 120 sec.

TABLE 1

| | PCR Primers | | | |
|---|---|---|---|---|
| | Forward Primer | | Reverse Primer | |
| Gene | Sequence (5'-3') | SEQ ID NO: | Sequence (5'-3') | SEQ ID NO: |
| 14-3-3 | CTCTGAAAGCTGCCAC CTGCGCA | 3 | CTCCTTTCTGCACCCT CTTCCTTTAGC | 4 |
| CD14F | GAGGATATTCAGGGAC TTGGATTTG | 5 | GGTCGATAAGTCTTCC GAACCTCT | 6 |
| HOXA2 | TGGGCCCGGGGCGCA GACTCTGG | 7 | GCAGGAGAAAGGAGC AGAGGAA | 8 |
| PGK1 | CGTCCAGCTTGTCCAG C | 9 | ATTCCAGGGGTTGGG GT | 10 |

Table 2 presents the Ct values (which is the cycle that the fluorescence exceeds a defined threshold value) for each amplified product using the different templates. The 'no template' control reactions (for every primer pair) produced no amplicons. In general, the addition of the anionic detergent (poly (ethylene glycol) 4-nonylphenyl 3-sulfopropyl ether potassium salt) yielded lower Ct values at higher dilutions than the Tween 20-containing amplification mixes.

TABLE 2

| Amplification with Tween 30 or Anionic Detergent. | | | | | | | | | | |
|---|---|---|---|---|---|---|---|---|---|---|
| | | Mse-I digested DNA | | | | | Intact DNA | | | |
| | | 14-3-3 | CD14F | HoxA2 | PGK1 | | 14-3-3 | CD14F | HoxA2 | PGK1 |
| Tween 20 | 400 ng | 21.15 | 31.11 | 23.54 | 24.82 | 25 ng | 24.04 | 33.66 | 24.5 | 25.6 |
| | 40 ng | 26.18 | No Ct | 28.7 | 30.8 | 2.5 ng | 29.29 | No Ct | 29.59 | 31.26 |
| | 4 ng | 29.22 | No Ct | 31.95 | No Ct | 0.25 ng | No Ct | No Ct | 33.99 | No Ct |

TABLE 2-continued

Amplification with Tween 30 or Anionic Detergent.

|  |  | Mse-I digested DNA | | | | | Intact DNA | | | |
|---|---|---|---|---|---|---|---|---|---|---|
|  |  | 14-3-3 | CD14F | HoxA2 | PGK1 |  | 14-3-3 | CD14F | HoxA2 | PGK1 |
| Efficiency |  | 61 | — | 54 | 16 |  | 26 | — | 37 | 20 |
| Anionic | 400 ng | 21.17 | 30.15 | 22.27 | 23.17 | 25 ng | 24.31 | 28.72 | 23.33 | 23.62 |
|  | 40 ng | 24.86 | 34.72 | 26.47 | 27.95 | 2.5 ng | 27.88 | 33.98 | 26.92 | 28.33 |
|  | 4 ng | 28.65 | No Ct | 29.96 | 31.38 | 0.25 ng | 30.8 | No Ct | 30.41 | 31.59 |
| Efficiency |  | 75 | 42 | 69 | 58 |  | 105 | 26 | 86 | 63 |

The efficiency of amplification was derived from the slopes of the serially diluted template amplification plots (dilutional efficiency), and the percent efficiency is also presented in Table 2. For each amplicon, the anionic surfactant formulation had a higher efficiency than the corresponding Tween 20 formulation. Of the three amplicons for which efficiencies could be calculated for both detergent formulations, the anionic surfactant samples had an average of 67.3% and 84.7% efficiency for the digested and intact templates, respectively, whereas the Tween 20 samples had an average of 43.7% and 31% efficiency for the digested and intact templates, respectively.

Individual reaction efficiencies were calculated in an effort to explore the nature of the dilutional efficiency effects. Reaction efficiencies were calculated using the fold fluorescence change of each reaction using the fluorescence measurement of the cycles immediately following the Ct (efficiency=sum (Fc/Fc-1)n/2n where Fc is the fluorescence at cycle c, Fc-1 is the fluorescence at cycle c-1 and n is the number of cycle ratios used. When possible, three cycle ratios were used to calculate the reaction efficiency. As shown in Table 3, the percent of amplification efficiency was independent of formulation and initial template concentration. These data suggest that the efficiency depended upon the initial priming and/or primer extension. That is, reactions with lower amounts of template were less efficiently primed or initiated in the presence of Tween 20 than in the presence of the anionic surfactant. Once the amplification process began, however, the reaction efficiencies were detergent independent.

Example 4

Anionic Detergent Improves Specificity of Amplification

To determine whether amplification in the presence of the anionic detergent, poly (ethylene glycol) 4-nonylphenyl 3-sulfopropyl ether potassium salt, produced less non-specific products, formulations comprising Tween 20 were compared to an anionic detergent formulation. Primers (see Table 4) were designed to amplify a 352 by fragment (BsrGIO) and a 360 by fragment (SacIO) in human genomic DNA. The reactions (50 µl) contained 0.5 pg HEK293 genomic DNA, 50 µmol primers, 1×PCR Buffer, 0.2 mM dNTPs, 0.05 U/µL Taq, and 4% DMSO. Thermocycling parameters were 94° C. for 2 min, 30 cycles of 94° C. for 20 sec, 58° C. for 30 sec, and 72° C. for 80 sec, a final extension at 72° C. for 10 min, and a 4° C. hold.

TABLE 4

PCR Primers

|  | Forward Primer | | Reverse Primer | |
|---|---|---|---|---|
|  | Sequence (5'-3') | SEQ ID NO: | Sequence (5'-3') | SEQ ID NO: |
| BsrGIO | TGCATATTAGTGATAAGGATACAGGTTCTG | 11 | CGCCCGGCTAATTTTGTATTTT | 12 |
| SacIO | GACCAGCCTGGGCAACACAGCAAT | 13 | AGGCTGGGCATGGTGACTCAAG | 14 |

TABLE 3

Reaction Efficiencies (%)

|  |  | MseI digested DNA | | | | | Intact DNA | | | |
|---|---|---|---|---|---|---|---|---|---|---|
|  |  | 14-3-3 | CD14F | HoxA2 | PGK1 |  | 14-3-3 | CD14F | HoxA2 | PGK1 |
| Tween 20 | 400 ng | 100 | 97 | 108 | 106 | 25 | 102 | 127 | 108 | 104 |
|  | 40 ng | 104 | * | 109 | 97 | 2.5 | 102 | * | 100 | 97 |
|  | 4 ng | 106 | * | 99 | * | 0.25 | * | * | 92 | * |
| Anionic | 400 ng | 101 | 99 | 100 | 97 | 25 | 102 | 99 | 104 | 98 |
|  | 40 ng | 107 | 92 | 101 | 102 | 2.5 | 115 | 124 | 102 | 101 |
|  | 4 ng | 103 | * | 99 | 97 | 0.25 | 98 | * | 102 | 97 |

* No amplification product

Aliquots of each sample were run on an agarose gel (FIG. 3). There were fewer non-specific, secondary amplification products in reactions with anionic detergent formulations (lanes A) than with standard Tween 20 formulations (lanes T and R). This finding raises the possibility that there may be a multimolecular complex comprising template, primer, detergent, and enzyme, and it is possible that the anionic detergent increased the coulombic repulsion between template/primers and the detergent.

What is claimed is:

1. A composition, the composition comprising a thermostable DNA polymerase and an anionic detergent selected from the group consisting of poly(ethylene glycol) 4-nonylphenyl 3-sulfopropyl ether potassium salt; poly(ethylene glycol) monolaurate; polyoxyethylene(150)dinonylphenyl ether; and nonyl nonoxynol-15 phosphate.

2. The composition of claim 1, wherein the DNA polymerase in the composition retains enzymatic activity for at least 40 days at 25° C.

3. The composition of claim 1, wherein the DNA polymerase is from a thermophilic bacteria selected from the group consisting of *Thermus flavus, Thermus ruber, Thermus thermophilus, Bacillus stearothermophilus, Thermus aquaticus, Thermus lacteus, Thermus rubens*, and *Methanothermus fervidus*.

4. The composition of claim 1, wherein the DNA polymerase is Taq and the anionic detergent is poly(ethylene glycol) 4-nonylphenyl 3-sulfopropyl ether potassium salt.

5. The composition of claim 1, wherein the DNA polymerase is Taq and is present at a concentration from about 0.1 unit/μL to about 5 unit/μL; and the detergent is present at a concentration from about 0.001% to about 5% by weight.

6. The composition of claim 1, further comprising a reducing agent.

7. The composition of claim 1, further comprising a buffering agent that maintains the composition at a pH of from about 6 to about 9, wherein the buffering agent is selected from the group consisting of MOPS, HEPES, TAPS, Bicine, Tricine, TES, PIPES, MES, or a Tris.

8. The composition of claim 1, further comprising a mixture of dNTPs selected from the group consisting of dATP, dCTP, dGTP and dTTP.

9. The composition of claim 1, further comprising a salt selected from the group consisting of potassium chloride, sodium chloride, magnesium chloride, calcium chloride and lithium chloride.

10. The composition of claim 1, further comprising an agent that increases the efficiency of PCR selected from the group consisting of dimethyl sulfoxide, formamide, and betaine.

11. The composition of claim 1, wherein the anionic detergent is poly(ethylene glycol) 4-nonylphenyl 3-sulfopropyl ether potassium salt.

12. A kit for amplifying DNA in a thermal cycling process, the kit comprising a thermostable DNA polymerase and an anionic detergent selected from the group consisting of poly (ethylene glycol) 4-nonylphenyl 3-sulfopropyl ether potassium salt, poly(ethylene glycol) monolaurate, polyoxyethylene(150)dinonylphenyl ether, and nonyl nonoxynol-15 phosphate.

13. The kit of claim 12, wherein the anionic detergent is poly(ethylene glycol) 4-nonylphenyl 3-sulfopropyl ether potassium salt.

14. The kit of claim 12, further comprising a reducing agent, a buffering agent, and a mixture of dNTPs selected from the group consisting of dATP, dCTP, dGTP, and dTTP.

* * * * *

```
                        SEQUENCE LISTING

<160> NUMBER OF SEQ ID NOS: 14

<210> SEQ ID NO 1
<211> LENGTH: 24
<212> TYPE: DNA
<213> ORGANISM: Artificial
<220> FEATURE:
<223> OTHER INFORMATION: PCR PRIMERS

<400> SEQUENCE: 1
tggatacccg tcgtggctct aatt                                          24

<210> SEQ ID NO 2
<211> LENGTH: 24
<212> TYPE: DNA
<213> ORGANISM: Artificial
<220> FEATURE:
<223> OTHER INFORMATION: PCR PRIMERS

<400> SEQUENCE: 2
cttctttcgt ccccgtcagg ctga                                          24

<210> SEQ ID NO 3
<211> LENGTH: 23
<212> TYPE: DNA
<213> ORGANISM: Artificial
<220> FEATURE:
<223> OTHER INFORMATION: PCR PRIMERS

<400> SEQUENCE: 3
ctctgaaagc tgccacctgc gca                                           23

<210> SEQ ID NO 4
<211> LENGTH: 27
<212> TYPE: DNA
<213> ORGANISM: Artificial
<220> FEATURE:
<223> OTHER INFORMATION: PCR PRIMERS

<400> SEQUENCE: 4
ctcctttctg caccctcttc ctttagc                                       27

<210> SEQ ID NO 5
<211> LENGTH: 25
<212> TYPE: DNA
<213> ORGANISM: Artificial
<220> FEATURE:
<223> OTHER INFORMATION: PCR PRIMERS

<400> SEQUENCE: 5
gaggatattc agggacttgg atttg                                         25

<210> SEQ ID NO 6
<211> LENGTH: 24
<212> TYPE: DNA
```

<213> ORGANISM: Artificial
<220> FEATURE:
<223> OTHER INFORMATION: PCR PRIMERS

<400> SEQUENCE: 6
ggtcgataag tcttccgaac ctct                24

<210> SEQ ID NO 7
<211> LENGTH: 23
<212> TYPE: DNA
<213> ORGANISM: Artificial
<220> FEATURE:
<223> OTHER INFORMATION: PCR PRIMERS

<400> SEQUENCE: 7
tgggcccggg gcgcagactc tgg                23

<210> SEQ ID NO 8
<211> LENGTH: 22
<212> TYPE: DNA
<213> ORGANISM: Artificial
<220> FEATURE:
<223> OTHER INFORMATION: PCR PRIMERS

<400> SEQUENCE: 8
gcaggagaaa ggagcagagg aa                22

<210> SEQ ID NO 9
<211> LENGTH: 17
<212> TYPE: DNA
<213> ORGANISM: Artificial
<220> FEATURE:
<223> OTHER INFORMATION: PCR PRIMERS

<400> SEQUENCE: 9
cgtccagctt gtccagc                17

<210> SEQ ID NO 10
<211> LENGTH: 17
<212> TYPE: DNA
<213> ORGANISM: Artificial
<220> FEATURE:
<223> OTHER INFORMATION: PCR PRIMERS

<400> SEQUENCE: 10
attccagggg ttggggt                17

<210> SEQ ID NO 11
<211> LENGTH: 30
<212> TYPE: DNA
<213> ORGANISM: Artificial
<220> FEATURE:
<223> OTHER INFORMATION: PCR PRIMERS

<400> SEQUENCE: 11
tgcatattag tgataaggat acaggttctg                30

<210> SEQ ID NO 12
<211> LENGTH: 22
<212> TYPE: DNA
<213> ORGANISM: Artificial
<220> FEATURE:
<223> OTHER INFORMATION: PCR PRIMERS

<400> SEQUENCE: 12
cgcccggcta attttgtatt tt                22

```
<210> SEQ ID NO 13
<211> LENGTH: 24
<212> TYPE: DNA
<213> ORGANISM: Artificial
<220> FEATURE:
<223> OTHER INFORMATION: PCR PRIMERS

<400> SEQUENCE: 13
gaccagcctg ggcaacacag caat                                              24

<210> SEQ ID NO 14
<211> LENGTH: 22
<212> TYPE: DNA
<213> ORGANISM: Artificial
<220> FEATURE:
<223> OTHER INFORMATION: PCR PRIMERS

<400> SEQUENCE: 14
aggctgggca tggtgactca ag                                                22
```